(12) United States Patent
Koc et al.

(10) Patent No.: US 11,046,003 B2
(45) Date of Patent: Jun. 29, 2021

(54) METHOD FOR THREE DIMENSIONAL PRINTING OF HETEROGENEOUS STRUCTURES

(71) Applicant: SABANCI ÜNIVERSITESI, Istanbul (TR)

(72) Inventors: Bahattin Koc, Istanbul (TR); Navid Khani, Istanbul (TR); Ali Nadernezhad, Istanbul (TR)

(73) Assignee: SABANCI UNIVERSITESI, Istanbul (TR)

( * ) Notice: Subject to any disclaimer, the term of this patent is extended or adjusted under 35 U.S.C. 154(b) by 442 days.

(21) Appl. No.: 16/305,061

(22) PCT Filed: Jun. 21, 2016

(86) PCT No.: PCT/TR2016/050188
§ 371 (c)(1),
(2) Date: Nov. 28, 2018

(87) PCT Pub. No.: WO2017/222480
PCT Pub. Date: Dec. 28, 2017

(65) Prior Publication Data
US 2020/0238621 A1  Jul. 30, 2020

(51) Int. Cl.
*B29C 64/314* (2017.01)
*B33Y 10/00* (2015.01)
(Continued)

(52) U.S. Cl.
CPC .......... *B29C 64/314* (2017.08); *B29C 64/118* (2017.08); *B33Y 10/00* (2014.12);
(Continued)

(58) Field of Classification Search
None
See application file for complete search history.

(56) References Cited

U.S. PATENT DOCUMENTS

| | | | | |
|---|---|---|---|---|
| 5,312,757 A * | 5/1994 | Matsuyama | ............ | B01L 3/021 422/105 |
| 8,808,625 B2 * | 8/2014 | Aoki | ..................... | B01L 3/0241 422/81 |
| 2015/0073061 A1 * | 3/2015 | Bauer | ................. | B81C 1/00119 516/21 |

FOREIGN PATENT DOCUMENTS

| | | |
|---|---|---|
| EP | 2679669 A1 | 1/2014 |
| WO | 2011001185 A1 | 1/2011 |
| WO | 2015073944 A2 | 5/2015 |

OTHER PUBLICATIONS

Luiz E Bertassoni et al. "Direct-write bioprinting of cell-laden methacrylated gelatin hydrogels", Biofabrication, vol. 3, No. 2. Apr. 3, 2014. p. 024105.

(Continued)

*Primary Examiner* — Matthew J Daniels
*Assistant Examiner* — Paul Spiel
(74) *Attorney, Agent, or Firm* — Bayramoglu Law Offices LLC (57) ABSTRACT

A method for automatic printing of a three dimensional heterogeneous structure in accordance with a computer-aided design procedure, including the steps of: aspirating a first portion consisting of a first material (M1) in liquid form, from a first liquid container into a capillary (C); aspirating a second portion consisting of a second material (M2) in liquid form different than the first material (M1), from a second liquid container into said capillary (C), such that the first portion and the second portion constitute longitudinally different parts of a longitudinally heterogeneous filament (F) encompassed by the capillary (C); and extraction of the filament (F) from the capillary (C) thus laying it as a portion of a printed layer.

20 Claims, 6 Drawing Sheets

(51) Int. Cl.
   *B29C 64/118*  (2017.01)
   *B33Y 70/10*  (2020.01)
   *B29K 507/04*  (2006.01)

(52) U.S. Cl.
   CPC .......... *B33Y 70/10* (2020.01); *B29K 2039/06* (2013.01); *B29K 2507/04* (2013.01); *B29K 2995/0005* (2013.01)

(56) References Cited

OTHER PUBLICATIONS

Chimate Chetan et al. "Pressure assisted multi-syringe single nozzle deposition system for manufacturing of heterogeneous tissue scaffolds", International Journal of Advanced Manufacturing Technology, Sprinager Verlag, London, vol. 75, No. 1, Jul. 16, 2014, p. 317-330.
K H Kang, L A Hockaday and J T Butcher, "Quantitative optimization of solid freeform deposition of aqueous hydrogels", Biofabrication 5, 035001 (2013).
Hardin, J. O. et al., "Microfluidic Printheads for Multimaterial 3D Printing of Viscoelastic Inks", Advanced Materials, 2015.
Lewitus, D. Y. et al. "Biohybrid carbon nanotube/agarose fibers for neural tissue engineering", Advanced functional materials, 2011.
Zhao, W. et al. "A methodology to analyse and simulate mechanical characteristics of poly (2-hydroxyethyl methacrylate) hydrogel", Polymer International, 62, 1059-1067, 2013.
Schneider, C. A., et al., "NIH Image to ImageJ: 25 years of image analysis". Nature methods, 9, 671-675, 2012.

* cited by examiner

METHOD FOR THREE DIMENSIONAL PRINTING OF HETEROGENEOUS STRUCTURES

CROSS REFERENCE TO THE RELATED APPLICATIONS

This application is the national phase entry of International Application No. PCT/TR2016/050188, filed on Jun. 21, 2016, the entire contents of which are incorporated herein by reference.

TECHNICAL FIELD

The present invention relates to a method for automatic 3D printing, more specifically to a printing method of heterogeneous and/or multi-functional structures in accordance with a suitable CAD procedure.

BACKGROUND

Current 3D printing methods are mostly limited to fabricating parts with one type of material or only provide one type of functionality. Available approaches in printing of heterogeneous three dimensional hydrogel structures using multiple nozzles include deposition of each ink at an edge (i.e. starting/ending point) of previously deposited material. This bears the risk of inaccuracy in deposition and also inducing gaps (i.e. structural defects), at the patterned segments' interface with the matrix.

Multi-material hydrogel deposition using extrusion-based approaches lack geometrical precision in preserving features of CAD models at sharp-edged regions. Even by optimization of the tool-path, sharp edges usually have rounded off shapes in continuous deposition of filaments.

Figure 1:
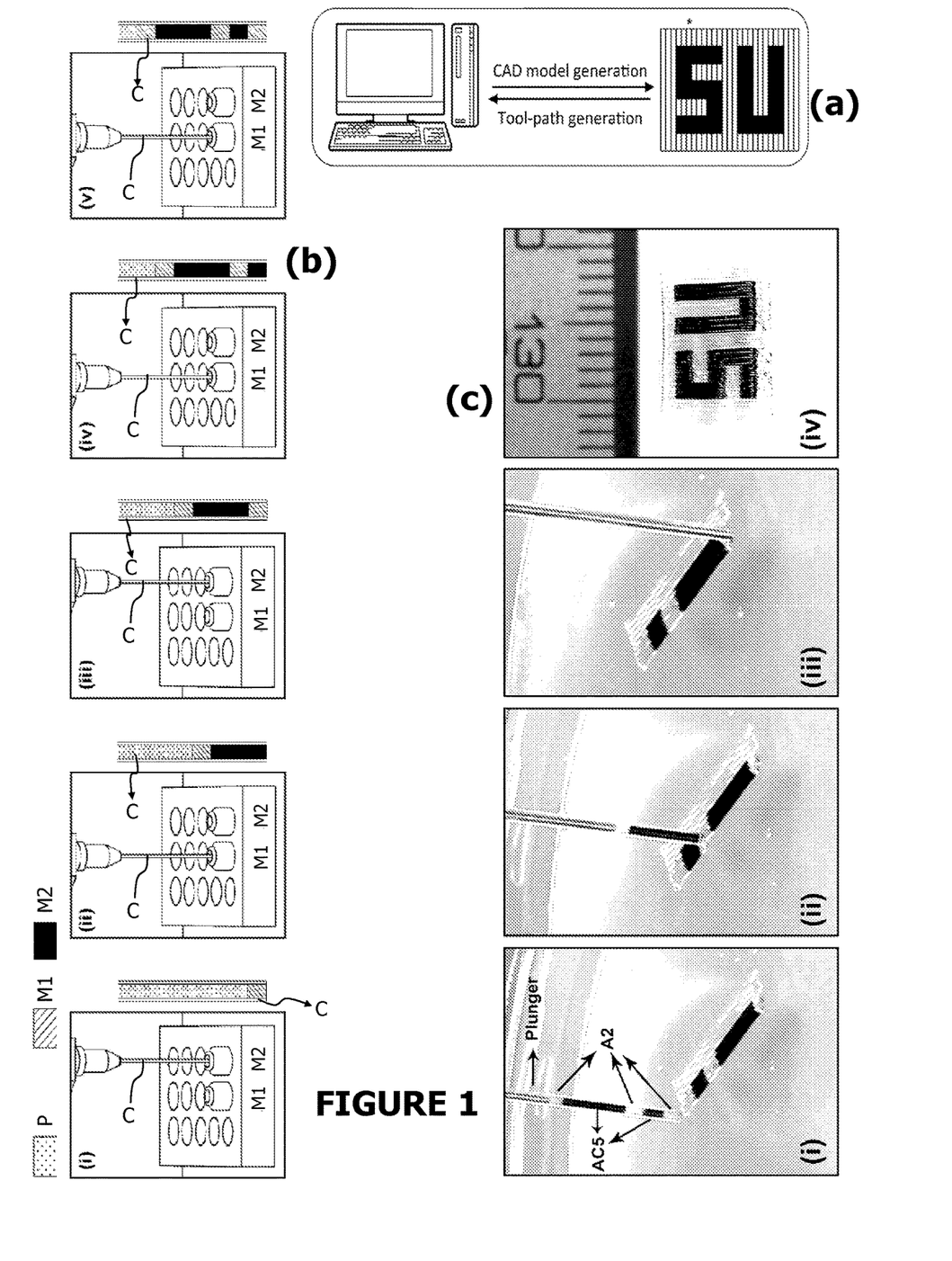
Figure 2:
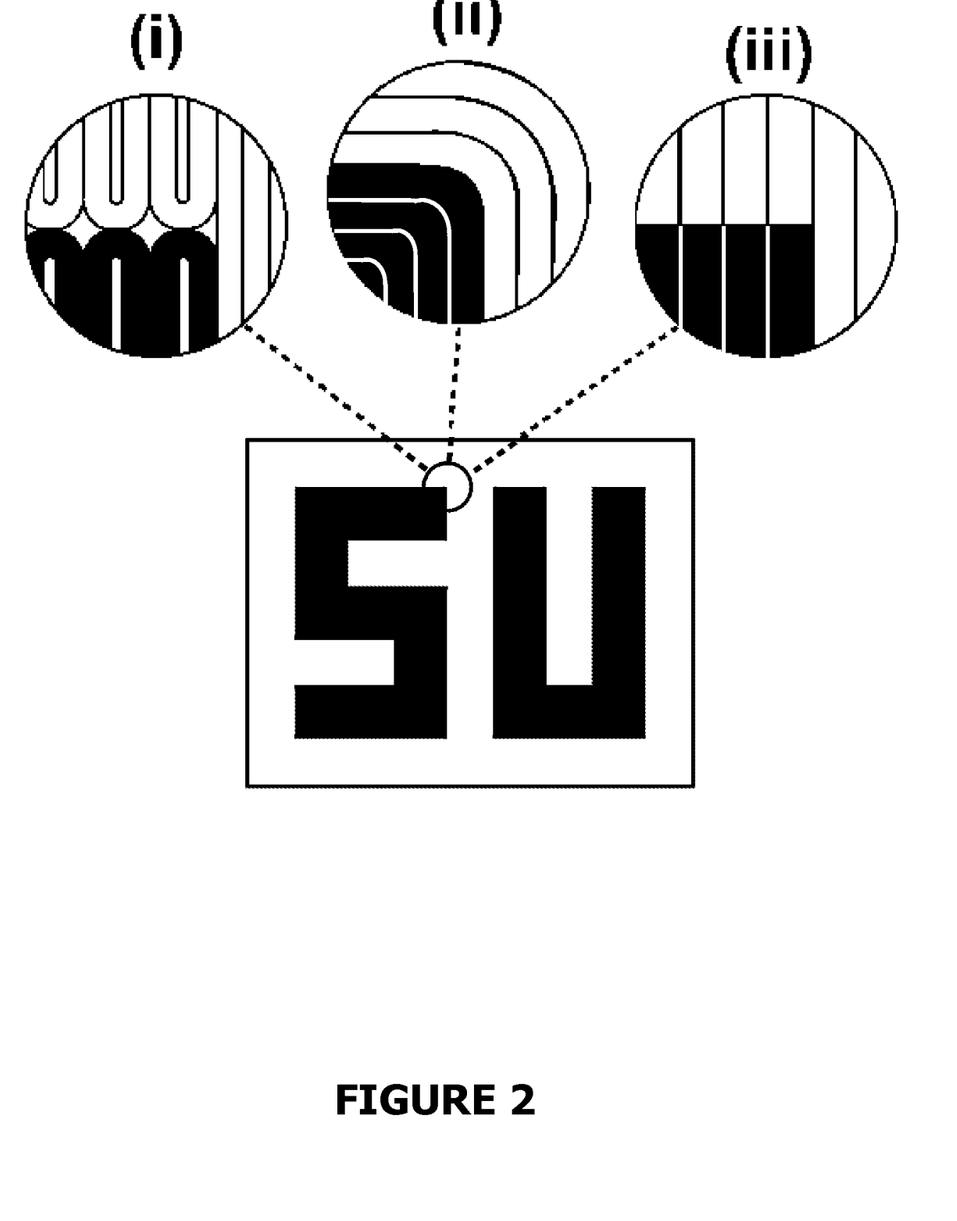
FIG. 2 schematically represents some possible tool-paths to produce a typical edge in pattern, (i) using a prior art method, (ii) using an alternative prior art method, and (iii) using the method according to the present invention.

Unwanted curvature at edges according to current tool-path designs (FIG. 1 (i) and (ii)) can be minimized by decreasing filament diameter even though exist certain limits are still present, beyond which printing can be considered practically impossible. Depending on the nozzle geometry and dispensing mechanism, printing time and shear stress at nozzle tip are affected by narrowing down the nozzle diameter, and this may negatively affect print quality. Furthermore, a quantitative study (Kang, K., Hockaday, L. & Butcher, J. Quantitative optimization of solid freeform deposition of aqueous hydrogels. Biofabrication 5, 035001 (2013)) on deposition parameters for printing from aqueous hydrogels, suggested that lower nozzle diameters will not necessarily provide better resolution. Shear stress induced by low nozzle diameters should also be strictly followed for avoidance from undesired changes in ink properties, especially for bio-inks employed in bioprinting.

Recently, Hardin et al. (Hardin, J. O. et al., Microfluidic Printheads for Multimaterial 3D Printing of Viscoelastic Inks, Advanced Materials (2015)) proposed a microfluidic printhead for continuous direct ink printing of heterogeneous structures with viscoelastic inks. According to the report, it is possible to print 1D, 2D and 3D heterogeneous structures with satisfying control on transition sharpness of subsequent layers of the printed object. Although said process is able to seamlessly switch between printing two different materials, this practice is only limited to viscoelastic inks. Viscosity has a crucial role in controlling the interface of transition between two different materials and decreasing the viscosity may decrease the sharpness of transition.

The WO 2011/001185 A1 discloses a method for printing of multiple portions of liquid materials different than each other, using a capillary. Here, subsequent portions of liquid materials are separated from each other by air segments, thereby preventing from contacting each other. Deposition of adjacent consecutive portions consisting of respective first and second liquid materials different from each other, requires purging of air separating said consecutive portions; therefore is only available with interruptions related to such purging steps.

SUMMARY

Primary object of the present invention is to overcome the abovementioned shortcomings of the prior art.

Another object of the present invention is provision of a method for printing of three dimensional heterogeneous and/or multi-functional objects.

Another object of present invention is provision of such method with high-fidelity in shaping heterogeneous corners within or at the printed objects.

The present invention proposes a method for automatic printing of a three dimensional heterogeneous structure in accordance with a computer-aided design procedure, comprising the steps of: aspirating a first portion consisting of a first material in liquid form, from a first liquid container into a capillary; aspirating a second portion consisting of a second material in liquid form different than the first material, from a second liquid container into said capillary, such that the first portion and the second portion constitute longitudinally different parts of a longitudinally heterogeneous filament encompassed by the capillary; and extraction of the filament from the capillary thus laying it as a portion of a printed layer.

BRIEF DESCRIPTION OF THE DRAWINGS

The figures, whose brief explanations are herewith provided, are solely intended for providing a better understanding of the present invention and are as such not intended to define the scope of protection or the context in which said scope is to be interpreted in the absence of the description.

FIG. 1 (a) schematizes the interrelation between computer aided design (CAD) model generation and the tool-path generation for 3D printing.

FIG. 1 (b) (i)-(v) schematizes formation of a heterogeneous and/or multi-functional longitudinal filament by aspiration of a first material (indicated as M1) from a first liquid container and of a second material (indicated as M2) from a second liquid container into a capillary (C) by moving a plunger (P) therethrough.

FIG. 1 (c) (i)-(iii) show time-lapse photographs taken whilst the filament is released from the capillary to form a part of an exemplary 3D printed object; and (iv) said exemplary object upon completion of a printed layer made of side-by-side released filaments.

DETAILED DESCRIPTION OF THE EMBODIMENTS

Referring now the figure outlined before, the present invention proposes a method for automatic printing of a three dimensional (3D) heterogeneous structure in accordance with a computer-aided design procedure. The method corresponds to multi-material deposition of shapeable longitudinal structures (as filaments, F) based on an aspiration-on-demand protocol. Different heterogeneously patterned 3D objects with varying chemical, electrical, mechanical and biological properties (or functions) can be printed with the method according to the present invention.

The method according to the present invention comprises the following steps:
(a) aspirating a first portion consisting of a first material (M1) in liquid form, from a first liquid container into a capillary (C),
(b) aspirating a second portion consisting of a second material (M2) in liquid form different than the first material (M1), from a second liquid container into said capillary (C), such that the first portion and the second portion constitute longitudinally different parts of a longitudinally heterogeneous filament (F) encompassed by the capillary (C); and
(c) extraction of the filament (F) from the capillary (C) thus laying it as a portion of a printed layer.

Figure 6:
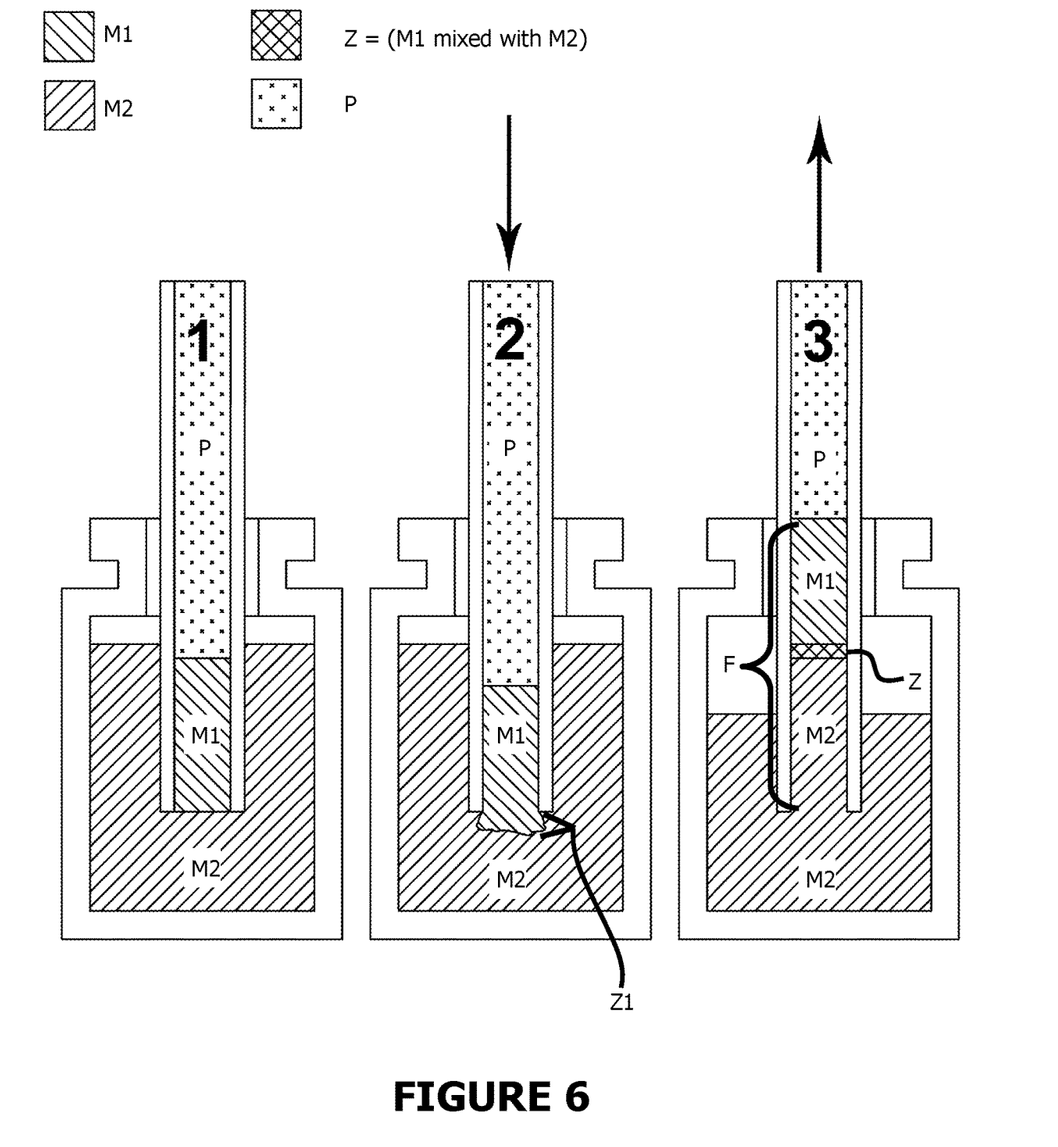
FIG. 6 schematically represents the aspiration of the second portion such that a filament (F) with a transition zone (Z) is formed in the capillary (C).

An alternative of the method according to the present invention further comprises the following steps between the above steps (a) and (b):
(i) partly extracting of the first portion into the second liquid container, and keeping the extracted part (Z1) therein for a time period, then
(ii) aspirating the extracted part back into the capillary;
such that a transition zone (Z) consisting of a mixture of the first material (M1) and the second material (M2) is obtained along the extracted part (Z1). This alternative is schematically visualized in the accompanying FIG. 6.

In an alternative of the method according to the present invention, the first material and the second material comprise thermally cross-linked hydrogel. Alternatively, the first material and/or the second material is selected to be such that it is in liquid form when aspirated, and then is converted into a gel form (i.e. gelated) by subjecting it to UV light, temperature or chemical agents. A person skilled in the art would be able to select a method of gelation among those mentioned above, and select suitable materials to be gelated in order to perform this alternative according to the present invention.

In the method according to the present invention, one or both of the first material and the second material may comprise electrically conductive material.

In the method according to the present invention, one or both of the first material and the second material may comprise carbon nanotubes.

In the method according to the present invention, one or both of the first material and the second material may be a bio-ink by comprising live cells or active biomolecules such as growth factors, proteins or drugs.

The method according to the present invention may comprise controlling of the temperature at the capillary for maintaining the temperature of the filament around a set value.

The method may further comprise one or more additional steps of aspirating a further portion consisting of a further material in liquid form different than the second material, from a further liquid container into said capillary, such that the first portion, second portion and the further portion constitute longitudinally different parts of a longitudinally heterogeneous filament encompassed by the capillary. An integral filament having three or more longitudinally different portions can be obtained in accordance with such approach.

The process parameters and material-related (e.g. rheological) parameters can be tuned for optimization of flow behavior of the filament, and of diffusion behavior between the first and second materials for obtainment a desired length and contrast around the transition zone (Z). The length of transition zone (transition zone length, TZL) and the interface between the first and second portions can be controlled.

Several exemplary lab-scale experiments according to the method of the present invention are described below in detail. By giving said examples, it is solely intended to provide a better understanding of the present invention, and the examples as such are not intended to limit the scope of the appended claims.

EXAMPLES

Various model thermally cross-linked hydrogels based on agarose with different concentrations, compositions and bio-functionalities were printed to examine the method. A sequential aspiration-on-demand protocol which can be easily manipulated by CAD (computer-aided design) was employed. Physical properties of materials (inks) to be printed were considered in tuning process parameters such as process temperature, interfacial features in switching segments (i.e. portions of the filaments corresponding to the first and second materials); as well as functionality, stability and integrity of printed objects as products of the method.

Materials (inks) of different agarose concentrations and compositions were prepared and used in printing of patterned constructs, as shown in the Table 1. Agarose hydrogels with different concentrations were used as primary inks. The compositions were altered by employing various concentrations of single-walled carbon nanotubes (SWCNTs) embedded in agarose hydrogels. Bio-functionality of agarose ink was modified by including NIH 3T3 cells into the hydrogel matrix, which can also be referred to as cell laden bioink.

TABLE 1 ink formulations used in deposition of patterned constructs.

| Ink ID. | Agarose concentration (w/v %) | SWCNT concentration (w/v %) | NIH 3T3 cell concentration (w/v %) |
|---|---|---|---|
| A1 | 1 | 0 | 0 |
| A2 | 2 | 0 | 0 |
| A3 | 3 | 0 | 0 |

TABLE 1-continued ink formulations used in deposition of patterned constructs.

| Ink ID. | Agarose concentration (w/v %) | SWCNT concentration (w/v %) | NIH 3T3 cell concentration (w/v %) |
|---|---|---|---|
| A4 | 4 | 0 | 0 |
| A5 | 5 | 0 | 0 |
| AC1 | 2 | 0.01 | 0 |
| AC2 | 2 | 0.02 | 0 |
| AC3 | 2 | 0.03 | 0 |
| AC4 | 2 | 0.04 | 0 |
| AC5 | 2 | 0.05 | 0 |
| AS3 | 3 | 0 | 0 |
| A- NIH* | 3 | 0 | $1 \times 10^6$ |

*Low melting temperature agarose (sieve) was used as the primary hydrogel ink.

Deposition of a Complex Patterned Object by Altering Ink Composition:

In a typical printing session by the method according to the present invention, CAD models which are generated based on desired geometries to be printed and on segmented models thereof, are used to assign the aspiration sequences. The route followed by the capillary nozzle (tool-path) is generated according to the models (or modeled structures) and automatically translated to machine language with the aid of CAD software. Switching between different materials (for obtainment of a filament) is precisely controlled by considering materials reservoir temperatures and interfaces between two sequentially aspired materials in a filament (desired transition zone lengths (i.e. length of transition zone along the longitudinal axis of the capillary) for a desired materials contrast along a filament, and e.g. radial homogeneity at radial sections of longitudinal filaments). The former directly affects material viscosities while the latter determines the smoothness (as the opposite of the above-mentioned contrast) of transition zone (transient section between two neighboring segments or portions of different materials) and geometrical integrity in filaments to be deposited.

Since agarose based inks are thermally cross-linked hydrogels, viscosity was taken as a function of temperature, and gelation occurred as an irreversible thermal crosslinking process, except for AS3 and A-NIH inks in which the gelation was thermally reversible. Temperature plays a crucial role in determination of ink viscosity, and affects process parameters such as aspiration temperature and the timing between aspirations sequences; the latter was controlled by printer head speed. The speed of printer head (capillary nozzle) affects the viscosity of already aspirated ink since it determines the time duration wherein the glass capillary is out of ink's reservoir and is exposed to environment temperature. Viscosity and storage modulus of inks are dependent on temperature. Therefore in an alternative embodiment, temperature control around a desired set value (around the temperature values of materials reservoirs) can be applied to the printer head.

Temperature of inks reservoir was set to 50° C. at which all inks showed liquid like behavior and their viscosities were low enough to ease the aspiration. Cross-over points are considered as a function of agarose and SWCNT concentrations. Above cross-over temperatures, the contribution of liquid-like behavior on the rheology of mixtures was dominant and cross-over points can be considered as the turning point below which inks tend to show more elastic behavior. However, cross-over points in AC3 to AC5 inks increased dramatically compared to the same values in AC1 and AC2 inks. This increase in cross-over temperature can be attributed to the formation of SWCNT network in the mixture, indicating high performance of dispersion step during ink processing. Trends in viscosity profiles of AC3 to AC5 inks during cooling (the plateau region before drastic increase in viscosity) seemed to be similar to the other inks although the cross-over points shifted to higher temperatures. The consistency in viscosity profiles of hydrogel-SWCNT inks with the base agarose ink (A2) indicates the printability of their combination in the same processing temperature, regardless of the more elastic contribution in corresponding inks at a temperature span of about 10 degrees. Rheological data together with results of heat flow simulation during ink switching were used to adjust the printer head speed. Thermal simulations showed that the temperature drop during ink switching in previously aspirated ink can be maintained within an acceptable range at which gelation would not occur, and change in viscosity of inks is negligible.

The aspiration and extraction of the filaments into and out of the capillary were performed using a plunger travelling along the main axis of the capillary. In addition to process temperature, the plunger displacement during aspiration of multi-ink filaments should be handled carefully to make sure that deposited filament has high degree of structural and geometrical integrity at the interface between two neighboring segments where ink switching occurs. To investigate the quality of segments' assembly in aspiration of each filament, we introduced a parameter called the transition zone length (TZL). Transition zone between two sequenced segments is obtained by extrusion of a designated length of previously aspirated ink inside the next ink's reservoir (i.e. reservoir of the second material; second reservoir), just before commencing the next aspiration corresponding to aspiration of the second material. This results in formation of a tiny volume of two inks mixture, magnitude of which can be controlled by the plunger displacement corresponding to the TZL. Increase in TZL is observed by increasing the volume of extruded ink (length of the extruded part of the first material out of the capillary) inside the second reservoir before the next aspiration.

Extended TZL values will result in a smoother transition between two neighboring segments, and depending on desired output property (chemical, electrical, mechanical, or biological properties), TZL can be roughly controlled. However, due to the risk of contamination in ink reservoir and non-homogeneous nature of mixture at the interface, TZL is practically limited to several hundreds of micrometers. It should be noted that plunger speed during aspiration must be low enough to prevent from formation of turbulent ink flow, and at the same time, it should be high enough to keep the processing time reasonable.

In cases of the experiments, increasing plunger speed from 50 to 100 mm/min resulted in formation of radially non-homogeneous mixture of two inks at the interface. At increased plunger speed (aspiration rate), even by setting the plunger displacement at second stage of aspiration to zero (directly aspirating the second portion without partly extracting of the first portion), formation of a turbulent ink flow caused extension of TZL at the interface. A combination of large plunger displacement before aspiration and high aspiration rate resulted in generation of significantly non-homogeneous transition zone in orders of millimeters. Images taken by high-speed camera during deposition of a single segmented filament demonstrate that even by setting the plunger displacement at said extraction to zero, geometrical and structural integrity of filaments were preserved precisely at the switching interface and in the meantime, switching interface withstands the high shear and normal stresses at the tip (nozzle) of the capillary during deposition. This observation indicates the independence of filament geometrical integrity at switching interface from TZL, as far as two neighboring segments have been aspirated while they are still in the liquid (low viscosity) state.

Deposition of Hydrogel Inks with Geometrically Patterned Properties:

Several patterns were generated by altering chemical, mechanical, electrical, and biological properties of deposited structures. The printed pattern comprises several filaments each was composed of one or more segments of A2 and/or AC5 inks. Accurate translation of CAD geometry into machine codes and adaptation of process parameters to inks' physical properties resulted in obtaining near net shape object which is in good match with designed CAD model. Reliability of the present method in deposition of complex patterns using multi-inks with different compositions was evaluated by comparing deposited object with the respective CAD model. To demonstrate the ability to pattern the stiffness in printed constructs, hydrogel inks were first mechanically characterized using compression test to identify their stress-strain behavior. The response to applied normal force in hydrogel inks is demonstrated in stress-strain plots. Two regions of linear elastic and non-linear response to applied stress were observed and the maximum stress in strain-confined tests increased significantly by increasing agarose concentration from about 7 kPa to more than 117 kPa. Elastic moduli of inks were determined from small strain portion of stress-strain plots (up to 4% strain) in which samples showed linear elastic properties and they could be described by Hook's law. Values of Young's moduli as a function of agarose concentration were plotted. Broadness in range of stiffness values of inks with different agarose concentrations was employed to deposit objects with patterned stiffness properties.

A sample pattern of nested squares was printed by using four inks including A1 to A4 in which the concentration of agarose varied over 1 to 4 w/v %. To visualize the deposited pattern clearly, Young's modulus values of different regions of sample are plotted as well as a contour merging all segments. Young' modulus changed from 23.6±2.0 kPa in the outmost segment to 500.4±7.7 kPa in the square at the center.

Figure 3:
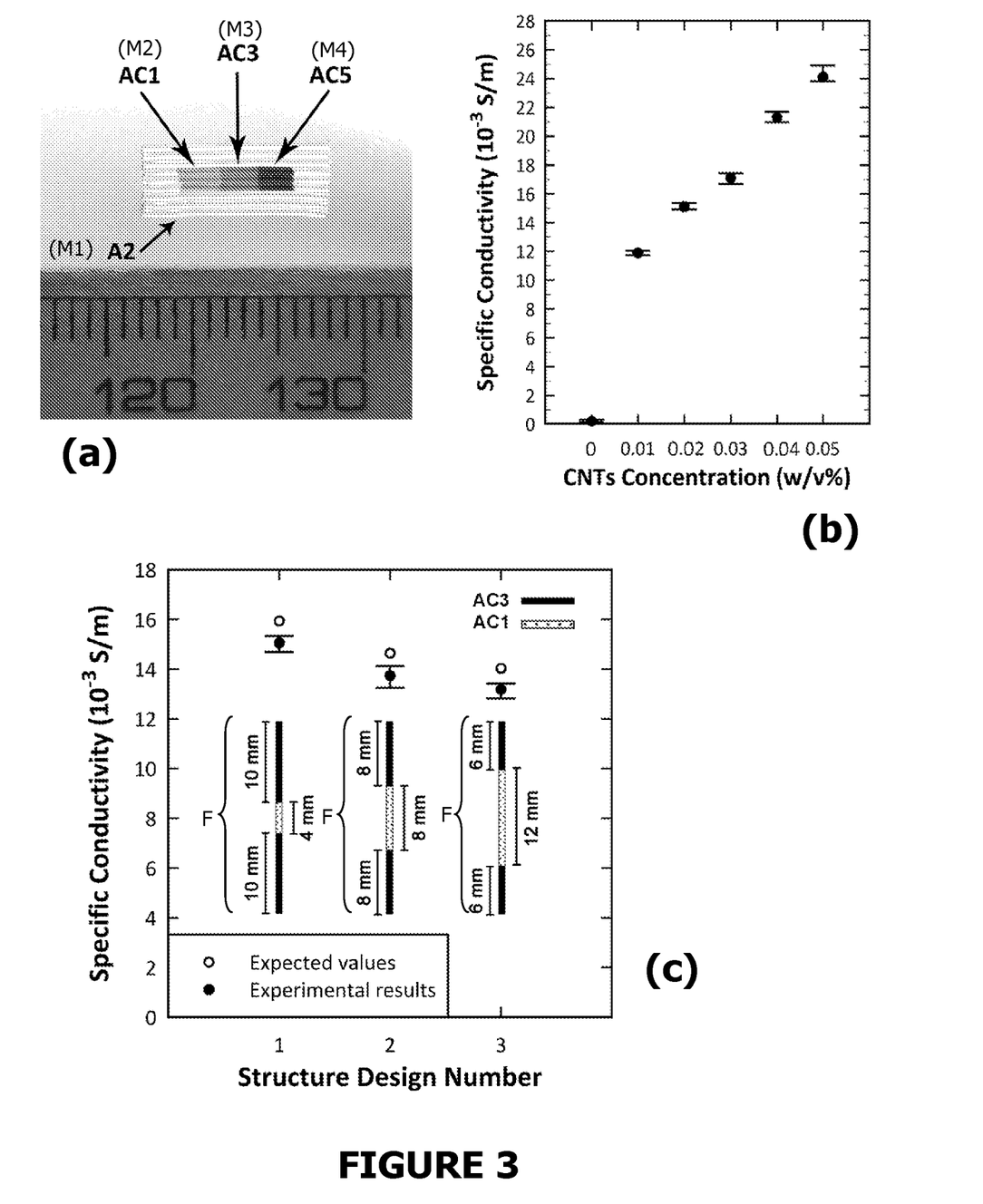
FIG. 3 shows (a) a photograph of a printed layer of filaments formed from materials with different carbon nanotubes (CNTs) concentrations; (b), graph showing the correlation between specific conductivity value of a filament portion and corresponding CNTs concentration in that portion; and (c), specific conductivities for different filament designs obtained by using different lengths of portions of different materials (i.e. AC3 and AC1 having different CNTs concentrations).

SWCNT embedded hydrogel inks were used to selectively pattern the electrical conductivity of deposited structures (as shown in FIG. 3). Specific conductivity of filaments composed of A2 (SWCNT concentration equals to zero) and AC1 to AC5 inks were plotted. Incorporation of SWCNTs in agarose enhanced the conductivity although this enhancement was not much significant compared to a previous study on agarose/CNT hydrogel nanocomposites (Lewitus, D. Y. et al. Biohybrid carbon nanotube/agarose fibers for neural tissue engineering. Advanced functional materials 21, 2624-2632 (2011)) since AC1 to AC5 inks had considerably low SWCNT concentrations which were not enough to induce noteworthy effects on electrical properties of matrix. However, this minor improvement of electrical conductivity can still be employed to pattern electrical properties along preferred directions in deposited structures. A simple rectangular hydrogel construct with patterned electrical properties was printed by using the combination of A2, AC1, AC3 and AC5 inks. A gradient pattern was deployed in the printed object in which specific conductivity increased gradually from one end to another. Matrix composed of A2 ink had a very low conductivity compared to the patterned segments of the object in the same ambient environment.

To demonstrate the ability of our method in deposition of heterogeneous biologically functional patterns, a combination of A-NIH and AS3 inks were used to produce a simple structure patterned with NIH-3T3 cells inside an agarose matrix. Temperature at which the bio-ink and AS3 ink were kept during printing was set to 38° C. to prevent from gelation of inks and in the meantime, keep the encapsulated cells alive. Ink (bio-ink) has shown liquid like behavior while it was kept at 38° C. in ink's reservoir. A sharp interface between cell laden and cell free segments of filaments, is evident while no structural defect is visible at the interface section. Cell viability did not change significantly prior and after printing compared to the starting cell pellets before preparation of A-NIH bio-ink. Comparison between viability of cells prior and after printing suggests that the printing process does not induce damage to cells. According to rheological data, low gelation temperature of AS3 ink (35° C. as determined by G'-G" cross-over point) and shear thinning behavior of inks have reduced the risk of damage to cells caused by high shear rates during aspiration. The Power Law (Oswald) model was used to quantify shear thinning behavior of two inks. Flow index values for both AS3 and A-NIH inks (n=0.3 and 0.26, respectively) and the trend of viscosity-shear rate profiles were almost the same, although A-NIH bio-ink showed less non-Newtonian behavior in lower shear rates. Viscosity dropped significantly by increasing shear rate. The cell viability remained almost the same in bio-ink reservoir (about 97%) and after printing (about 95%), when compared to the initial value thereof (about 98%) in cell suspension.

Preparation and Characterization of Inks and Printed Hydrogels:

Agarose inks (A1 to A5) were prepared by dissolving agarose powder (A9539, Sigma-Aldrich) in distilled water by using boiling water bath method provided by the producer. AS3 ink was prepared by autoclaving the mixture of low melting temperature agarose (Biozym Sieve 3:1) and 1× phosphate buffer saline (PBS, Hyclone by Thermo Scientific) for 2 hours. Aqueous suspension of 0.1 wt % single-wall carbon nanotubes (SWCNT) with 0.1 wt % Polyvinylpyrrolidone (PVP) supplied by OSCiAl was used to produce SWCNT embedded nanocomposite hydrogels. Adequate amounts of agarose powder were added to aqueous dispersions of SWCNTs kept in a boiling water bath and stirred vigorously for 30 minutes to completely melt agarose powders. Mixtures were sonicated for 30 minutes using a probe sonicator (Q700, QSonica) while the amplitude and pulse on/off interval were set to 50% and 5 seconds, respectively. Temperature was maintained at 80° C. during sonication. NIH 3T3 cells were used to prepare cell laden bio-ink. Cells were cultured in Dulbecco's Modified Eagle Medium (DMEM, Sigma) containing 10% fetal bovine serum (FBS, Sigma) and 1% penicillin-streptomycin (Gibco), passaged two times a week and incubated in humidified atmosphere containing 5% CO 2 at 37° C. To prepare cell laden bio-ink, cell cultures were washed with 1×PBS and trypsinized for 5 min followed by centrifuging at 1100 rpm for 5 min. Cell pellets were re-suspended in growth medium and counted with hemocytometer after staining with trypan blue (Sigma). The proper amount of cells was added to AS3 ink kept at 38° C. to obtain cell laden bio-ink with $1\times10^6$ cells/ml density.

Rheological properties of inks were investigated using Anton Paar MCR 302 rheometer (Anton Paar, Austria) using 25 mm diameter parallel plates configuration. Samples were subjected to oscillatory shear stress (strain=1%, frequency=1 Hz) during cooling down from 50 to 20° C. with 6° C./min ramp, and complex shear modulus and complex viscosity of samples were recorded. Rotational rheometry was used by applying a shear rate sweep from 0.01 to 100 (1/s) at 38° C. for AS3 and A-NIH inks. Angular frequency sweep from 0.1 to 10 rad/s was applied at 38° C. to determine network stability of AS3 and A-NIH inks.

Cylindrical gel samples with 25 mm diameter and 30 mm height from A1 to A5 inks were prepared to perform uniaxial compression testing with the designed experimental setup. Experimental setup included a dynamometer (Kistler 9256C1) placed on the lower plate which was interfaced with data acquisition software (LabVIEW, National Instruments) to log the measured force during compression. The upper plate was connected to a high resolution stepper motor. To minimize the effect of friction on the contact plates and prevent from sample barreling during compression, a water repellant silicon compound lubricant (Dow Corning) was used (as in Zhao, W. et al. A methodology to analyse and simulate mechanical characteristics of poly (2-hydroxyethyl methacrylate) hydrogel. Polymer International 62, 1059-1067 (2013)). A prestrain of 1% with the head speed of 1 mm/min was applied prior starting the measurements. Five samples of each ink formulation were uniaxially compressed while the maximum strain was confined to 15% and the compression rate was set to 2 mm/min. Compressive loads versus upper plate displacement were recorded for each sample and stress-strain plots were generated accordingly. Small strain portion of stress-strain plots (up to 4% strain) were considered as the linear segment of plots at which the samples were described by the Hook's law.

To measure the electrical properties of gels, single filaments of each corresponding ink were printed on a polystyrene petri dish and droplets of gallium/indium eutectic (Sigma-Aldrich) were placed on each end of filaments. Agilent U1273A handheld digital multimeter connected to Cascade PM5 Port Probe Station was used to measure the electrical resistance of each filament. Resistance values were recorded for 15 seconds in each measurement. Five samples were measured from each hydrogel ink and the mean values were reported.

Printing Hydrogel Structures:

A custom-built 3D printer was developed, which consists of a three-axis motion control stage with servo motors in each axis and a plunger based dispensing unit motorized by a high resolution stepper motor. Machine was controlled by a personal computer through Mach3 control system (Newfangled Solutions, USA). The printer was equipped with a temperature controlled heating/cooling unit which was designed to maintain inks at a desired temperature during printing. The deposition speed of filaments was set to 150 mm/min while the aspiration/extrusion speed of inks varied over 50 to 100 mm/min. The computer aided designs were developed using Rhino software (Robert McNeel & Associates) and the tool-paths were generated by using Rhinoscript.

Imaging of Printed Structures:

The studies on interface between different segments in printed filaments were done by using Carl-Zeiss LSM 710 inverted confocal microscope. Fluorescent microbeads with excitation wavelength of 405 nm (Createx Colors, USA) were used to selectively mark segments in each filament. To visualize the patterned segments in printed constructs including bio-ink, and also to quantify the viability of cells prior and after printing, the following cell staining protocols were fallowed. Cell viability prior printing (in cell suspension) was evaluated by using a trypan blue exclusion test and cells were visually examined and scored. Cell viability in cell laden bio-ink kept in ink's reservoir and within printed patterned constructs was assessed by applying a live/dead fluorescence assay just after printing. Printed constructs were first stained by incubating in 2 calcein-AM (Invitrogen, green fluorescence) and 0.5 μM propidium iodide (Invitrogen, red fluorescence) for 20 min at 37° C., followed by washing by 1×PBS for three times. Tiled z stacks were then captured by Carl-Zeiss LSM 710 inverted confocal microscope and the 3D reconstructed images were quantitatively analyzed by ImageJ software (in accordance with Schneider, C. A., et al., NIH Image to ImageJ: 25 years of image analysis. Nature methods 9, 671-675 (2012)). The 3D Object Counter plug-in for ImageJ was used to quantify the number of live/dead cells in 3D stacks. All the patterned samples were directly printed, stained and washed on the same glass-bottom petri dishes. To capture real-time images and videos during deposition of filaments a NX4-S2 high speed camera (Integrated Design Tools, IDT) coupled with the Infinity K2 DistaMax macro lens (Infinity Photo-Optical) was used and data were recorded and processed by Motion Studio software suite (Integrated Design Tools, IDT).

The significance of the present method besides its simple nature is the capability of manipulating 3D printing parameters to yield a broad range of functionalities in deposited object and tuning different properties of starting inks to obtain desired features. Mutual dependency of effective process parameters (such as temperature, aspiration rate and printer head speed) and physical properties of inks is evident by considering the effect of temperature on flow behavior of inks, i.e. viscosity-temperature profiles. A temperature framework could be established based on inks' composition to keep the starting materials at desired viscosities and also control the heat loss during ink switching at obtainment of the longitudinally heterogeneous filament. Hydrogel viscosity plays an effective role in determination of printing fidelity since it implicates the resistance of fluid to flow under applied stress.

The design of the dispensing system employed in the method and the deposition mechanism in which the ink(s) turn to gel from liquid state (e.g. inside the glass capillary), guarantees shape accuracy of deposited filaments since they are already viscous enough to retain their shape during deposition. By keeping the ink's reservoir temperature constant, ink viscosity variations could also be minimized during the aspiration. This means that applied shear stress can be controlled, which affects the aspiration of sequenced segments e.g. at prevention of generating radially non-homogeneous mixture of inks at the switching interface (or at a certain radial section corresponding to the transition zone). Moreover, applied stress can be monitored by controlling viscosity in shear-stress sensitive inks and depending on the range of available process temperatures; the output functionality of ink can be maximized. The viscosity of cell-laden hydrogels can preferably be controlled to optimize the applied pressure on encapsulated cells and maximize the viability in an extrusion based deposition system.

Preserving the dimensional accuracy of deposited pattern in hydrogel constructs was evident in the printed samples. From geometrical point of view, an edge can be defined as the interface between two neighboring segments with different properties. FIG. 1 provides a schematic comparison between two typical continuous tool-paths (i, ii) and the method proposed by the present application (iii) in printing of a sharp-edged corner. As we demonstrated before, integrating multiple inks in a single filament results in enhanced sharpness at the edges of patterned segments (schematically presented in FIG. 1 (iii)). However, this enhancement substantially depends on the pattern's geometry. Patterns which are defined as curved objects or consist of non-perpendicular edges (outline edges of patterned area itself, or the angle between extended outlines of patterned area and those of background/matrix) will turn to be as jaggy segments. The resolution of the pattern will depend on filament diameter; the smaller the filament diameter the higher resolution at the curved edges, although the technical limits in reaching smallest possible diameters will eventually determine the resolution of pattern. The aforementioned geometrically dependent limitation is considered as a challenge in current robotic dispensing based printing practices both in continuous and discrete deposition methods. Compared to conventional deposition system designs, the proposed method has the advantage of improving pattern resolution while retaining structural integrity of neighboring segments by merging multiple segments into a single deposited filament. Moreover, changing segmentation orientation is an alternative approach to minimize the number and length of jagged edges in the case of non-perpendicular pattern's edges.

Hydrogels, while they are in the liquid like form, have very low viscosity which makes them unsuitable to be processed by such nozzle designs to yield high dimensional accuracy and also acceptable print fidelity. Even though tuning flow behavior by altering the chemistry might be a possible option to extend the application of capillary nozzle type print-head designs to less viscous materials, our approach in assembling hydrogel segments with different compositions and functionalities inside the glass capillary, provides the opportunity to control transition sharpness precisely and effectively in processing of inks with low viscosity.

The capability of this method, in producing sharp-edged and at the same time highly integrated segments, provides the opportunity to selectively and continuously switch between different functionalities/properties in deposited structure. Structural integrity of two neighboring segments in each filament is especially important when the printed object is intended to have patterned mechanical properties or to be used under mechanical stress. The integrity of interface will improve load transfer along two segments which in turn will enhance the stability of object under mechanical loading. Moreover, the ability to create patterned hydrogel structures with different mechanical properties and high dimensional accuracy showed great promise for applications in the field of tissue engineering since it the researchers in the field know that the stiffness of scaffold/substrate can affect cell-biomaterial response and direct cell spreading, migration and differentiation.

Since incorporation of carbon nanostructures like carbon nanotubes, graphene, or other electrically conductive nanoparticles in a hydrogel matrix results in hydrogel nanocomposites with enhanced electrical properties and emerges new potentials and functionalities; patterning electrical properties with high dimensional accuracy is favorable in a wide range of applications such as sensors, conductive substrates, actuators and tissue engineering constructs. With the method according to the present invention, we were able to deposit electrically conductive patterns by altering the composition of hydrogel inks. Accordingly, we speculate that geometrically dependent electrical conductivity of patterned sections can be further used in combination with the ability to selectively pattern encapsulated cells in hydrogel matrices, which will result in selective improvement of cell signaling.

By increasing the complexity of CAD models especially in the case of anatomically mimicked structures in tissue engineering, intricacy of patterns will grow and features like hangover geometries will appear in CAD models which need to be supported temporarily. Depending on the final geometry and functionality of printed object, developing a self-supporting structure with good structural integrity is desirable. As demonstrated in the previous section, the present method is capable of producing biologically active patterns in a hydrogel matrix. Good stability of the interface in printed objects will result in enhanced mechanical durability of construct which is a critical issue in fabrication of large objects. Combination of structural integrity and patterned bio-functionality provides new opportunities in the development of self-supporting hydrogel constructs for regenerative tissue engineering applications.

The method according to the present invention has a great potential in producing heterogeneous objects with spatially controlled functionalities while preserving structural integrity at the switching interface (transition zone) between different segments (e.g. between the first portion and the second portion in a filament). Referring to the above examples, the method may introduce new opportunities in multi-material additive manufacturing in hydrogels for diverse applications such as biosensors, flexible electronics, tissue engineering and organ printing. The "heterogeneous objects" here may be multi-functional objects: by their different portions being able to have different functions due to being made of materials different from each other. With the method according to the present invention, heterogeneous and/or multi-functional objects can be directly printed from CAD models.

Figure 4:
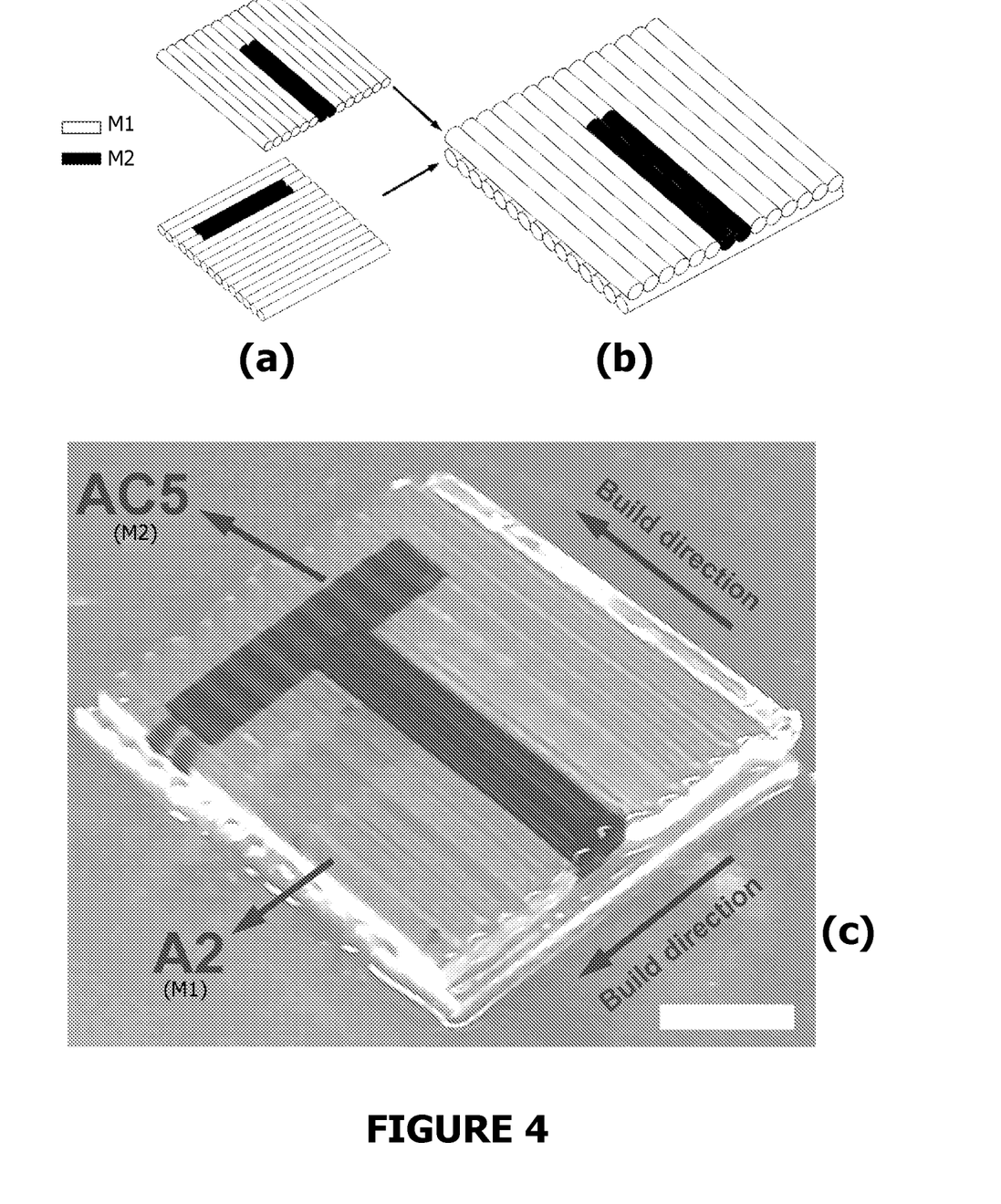
FIG. 4 shows (a) exploded view indicating different layers constituting a multilayer 3D printed object; (b) such 3D printed object with two layers of FIG. 4(a) on top of each other; and (c) a photograph of a multilayer 3D object printed with the method according to the present invention.
Figure 5:
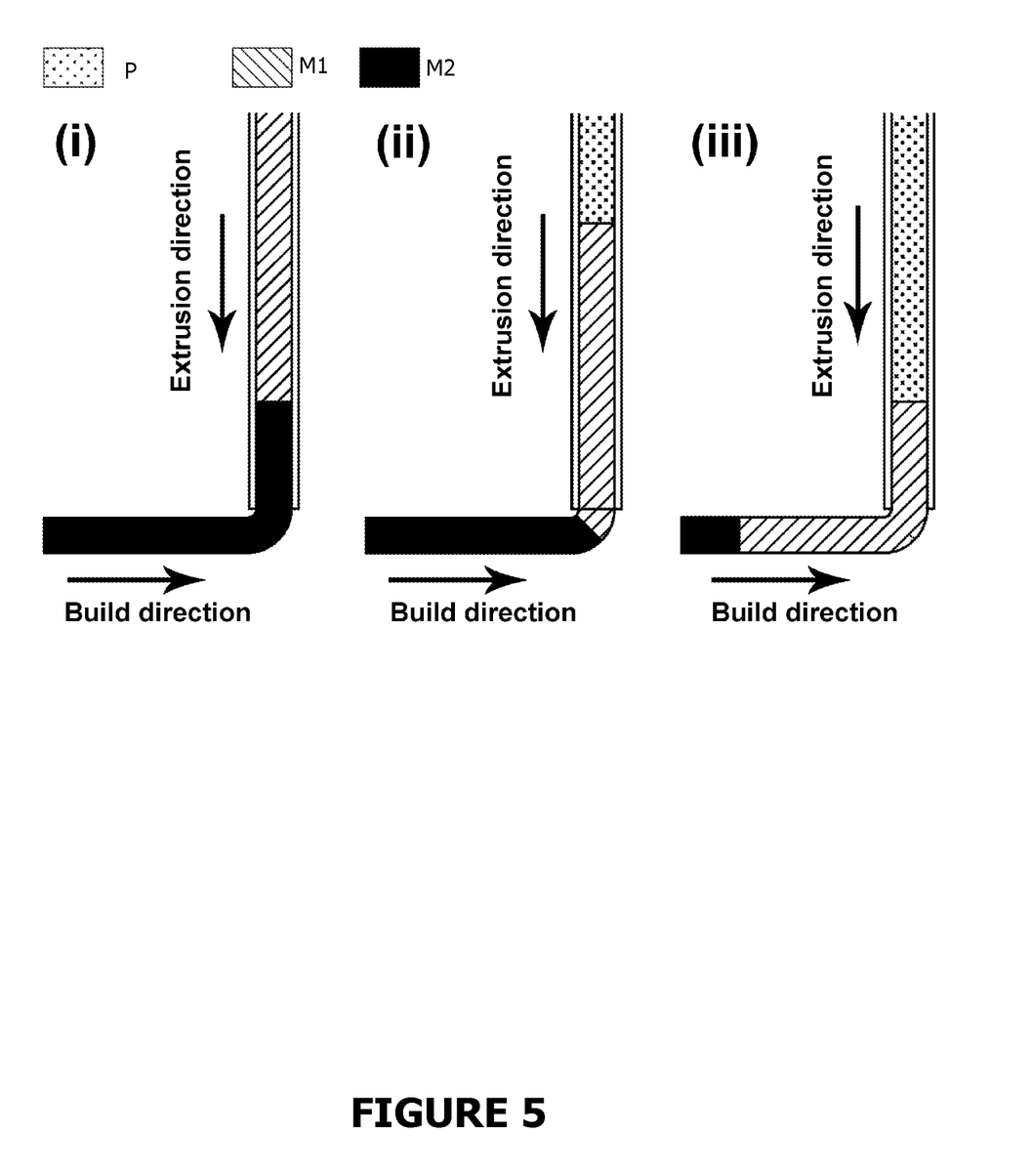
FIG. 5 schematizes releasing the filament to form a part of a printed layer.

For obtaining more complex 3D printed objects in accordance with the general inventive concept, the method according to the present invention may comprise laying multiple layers of longitudinal filaments on top of each other. An example therefore is visualized in the FIGS. 4 (b) and 4 (c).

Thus the following objects are achieved by the present invention:
overcoming the abovementioned shortcomings of the prior art,
provision of:
a method for printing of three dimensional heterogeneous and/or multi-functional objects.
such method with high-fidelity in shaping heterogeneous corners within or at the printed objects.

What is claimed is:
1. A method for automatic printing of a three dimensional heterogeneous structure in accordance with a computer-aided design procedure, comprising the following steps:
(a) aspirating a first portion consisting of a first material in liquid form, from a first liquid container into a capillary,
(b) aspirating a second portion consisting of a second material in liquid form different than the first material, from a second liquid container into the capillary, such that the first portion and the second portion constitute longitudinally different adjacent and consecutive parts of a longitudinally heterogeneous filament encompassed by the capillary; and
(c) extracting a filament from the capillary and laying the filament as a portion of a printed layer.

2. The method according to the claim 1, further comprising the following steps between the steps (a) and (b):
   (i) partly extracting a part of the first portion into the second liquid container, and keeping the extracted part therein for a time period, then
   (ii) aspirating the extracted part back into the capillary; such that a transition zone consisting of a mixture of the first material and the second material is obtained along the extracted part.

3. The method according to claim 2, wherein the first material and the second material comprise thermally cross-linked hydrogel.

4. The method according to claim 2, wherein the first material and/or the second material are in liquid form when aspirated, and then are converted into a gel form by subjecting to UV light, temperature or a chemical agent.

5. The method according to claim 2, wherein at least one of the first material or the second material comprise an electrically conductive material.

6. The method according to claim 2, wherein at least one of the first material or the second material comprise carbon nanotubes.

7. The method according to claim 2, wherein at least one of the first material and the second material are a bio-ink by comprising live cells or active bio-molecules selected from growth factors, proteins or drugs.

8. The method according to claim 2, further comprising controlling a temperature at the capillary for maintaining a temperature of the filament around a set value.

9. The method according to claim 1, wherein the first material and the second material comprise thermally cross-linked hydrogel.

10. The method according to claim 9, wherein at least one of the first material or the second material comprise an electrically conductive material.

11. The method according to claim 9, wherein at least one of the first material or the second material comprise carbon nanotubes.

12. The method according to claim 9, wherein at least one of the first material and the second material are a bio-ink by comprising live cells or active bio-molecules selected from growth factors, proteins or drugs.

13. The method according to claim 9, further comprising controlling a temperature at the capillary for maintaining a temperature of the filament around a set value.

14. The method according to claim 1, wherein the first material and/or the second material are in liquid form when aspirated, and then are converted into a gel form by subjecting to UV light, temperature or a chemical agent.

15. The method according to claim 1, wherein at least one of the first material or the second material comprise an electrically conductive material.

16. The method according to claim 1, wherein at least one of the first material or the second material comprise carbon nanotubes.

17. The method according to claim 1, wherein at least one of the first material and the second material are a bio-ink by comprising live cells or active bio-molecules selected from growth factors, proteins or drugs.

18. The method according to claim 1, further comprising controlling a temperature at the capillary for maintaining a temperature of the filament around a set value.

19. The method according to claim 1, further comprising one or more additional steps of aspirating a third portion consisting of a third material in liquid form different than the second material, from a third liquid container into the capillary, such that the first portion, second portion and the third portion constitute longitudinally different parts of a longitudinally heterogeneous filament encompassed by the capillary.

20. The method according to claim 1, further comprising laying multiple layers of longitudinal filaments on top of each other.

* * * * *